United States Patent [19]

Greene

[11] Patent Number: 4,742,000

[45] Date of Patent: May 3, 1988

[54] ANTIBODY TO HUMAN PROGESTERONE RECEPTOR AND DIAGNOSTIC MATERIALS AND METHODS

[75] Inventor: Geoffrey L. Greene, Chicago, Ill.

[73] Assignee: University of Chicago, Chicago, Ill.

[21] Appl. No.: 859,135

[22] Filed: May 2, 1986

[51] Int. Cl.$^4$ .................... G01N 33/53; G01N 33/577
[52] U.S. Cl. ......................................... 435/7; 424/85;
530/387; 530/413; 530/808; 530/809; 436/501;
436/503; 436/504; 436/513; 436/531; 436/548;
436/800; 436/801; 935/106; 935/108; 935/110
[58] Field of Search .................... 435/7; 436/501, 503,
436/504, 513, 531, 548, 800, 801; 530/387, 413,
808, 809; 424/85; 935/106, 108, 110

[56] References Cited

U.S. PATENT DOCUMENTS

| | | | |
|---|---|---|---|
| 4,433,056 | 2/1984 | Baranczuk | 436/503 |
| 4,454,232 | 6/1984 | Breglio et al. | 436/504 |
| 4,656,142 | 4/1987 | Jaouen et al. | 436/501 |

OTHER PUBLICATIONS

Edwards et al., J. Steroid Biochem., 20(6B) Jun. 1984, p. 1627 Abstract K4.
Logeat et al., Proc. Nat'l. Acad. Sci. USA, 80(21) 1983, 6456–9.
Logeat et al., Biochemistry, 24(4) Feb. 1985, 1029–35.
Sullivan et al., Endocrinology, 119(4) Oct. 1986, 1549–57.
Greene et al., Human Estrogen Receptor DNA, Science 231:1150–54, Mar. 7, 1986.
Greene, G. L., Biochemical Actions of Hormones, vol. XI, Chapter 8, pp. 207–239, Academic Press, 1984.
King et al., Monoclonal Antibodies Localize Oestrogen Receptor in the Nuclei of Target Cells. Nature 307:745–747, Feb. 23, 1984.
Hawkins, R. W., Receptors in the Management of Breast Cancer, British Journal of Hospital Medicine, pp. 160–164, Sep. 1985.
King et al., Comparison of Immunocytochemical and Steroid-Binding Assays for Estrogen Receptor in Human Breast Tumors, Cancer Research 45:293–304, Jan. 1985.
Heubner et al., An Automatic Multidimensional Chromatography System for Purification of Human Uterine Progesterone Receptor and Induction of Polyclonal Antibodies, J. Steroid Biochem. 24(1):207–214, 1986.
Greene, G. L., Gene Regulation by Steroid Hormones II, Chapter 12, pp. 191–200, Ed. A. K. Roy and J. H. Clark, Springer–Verag, NY 1983.
DeSombre et al., Estrogen Receptors, Antibodies and Hormone Dependent Cancer, Hormones and Cancer, p. 121, Alan R. Liss, Inc., New York, NY, 1983.
Nolan et al., A Sensitive Solid–Phase Enzyme Immunoassay for Human Estrogen Receptor, Current Controversies in Breast Cancer, pp. 433–441, University of Texas Press, Austin, TX, 1984.
Ringold, G. M., Steroid Hormone Regulation of Gene Expression, Ann. Rev. Pharmacol. Toxicol. 25:529–66, 1985.
Liao et al., Autoimmune Anti–Androgen–Receptor Antibodies in Human Serum, Proc. Natl. Acad. Sci. USA 82:8345–48, Dec. 1985.
Lippman, M. E., Management of Breast Cancer with Hormones and Drugs, Hospital Practice, pp. 119–127, May 15, 1986.
Welshons et al., Nuclear Localization of Unoccupied Receptors for Glucocorticoids, Estrogens, and Progesterone in GH$_3$ Cells, Endocrinology 117(5):2140–46, 1985.
DeSombre et al., Steroid Receptors in Breast Cancer, Special Report, The New England Journal of Medicine 301(18):1011–12, Nov. 1, 1979.
DeSombre, E. R., Breast Cancer: Hormone Receptors, Prognosis and Therapy, Clinics in Oncology 1(1):191–212, Mar. 1982.
Clark et al., Progesterone Receptors as a Prognostic Factor in Stage II Breast Cancer, The New England Journal of Medicine 309(22):1343–47, Dec. 1, 1983.
Eisen, H. J., An Antiserum to the Rat Liver Glucocorticoid Receptor, Proc. Natl. Acad. Sci. USA 77(7):3893–97, Jul. 1980.
Coffer et al., Antibodies to Human Myometrial Oestrogen Receptor, Biochemistry International 1(2):126–32, Aug. 21, 1980.
Logeat et al., Antibodies to Rabbit Progesterone Receptor: Crossreaction with Human Receptor, Proc. Natl. Acad. Sci. USA 78(3):1426–30, Mar. 1981.
Renoir et al., Antibodies Against Progesterone Receptor from Chick Oviduct, Eur. J. Biochem 127:81–86, 1982.
Moncharmont et al., Monoclonal Antibodies Against Estrogen Receptor: Interaction with Different Molecular Forms and Functions of the Receptor, Biochemistry 21:6916–21, 1982.
Okret et al., Monoclonal Antibodies Against the Rat Liver Glucocorticoid Receptor, Proc. Natl. Acad. Sci. USA 81:1609–13, Mar. 1984.
Pierce et al., Monoclonal Antibodies to Human Vitamin D–Binding Protein, Proc. Natl. Acad. Sci. USA 82:8429–33, Dec. 1985.
Edwards et al., Structural Analysis of Chicken Oviduct Progesterone Receptor Using Monoclonal Antibodies to the Subunit B Protein, Biochemistry 23:4427–35, 1984.

(List continued on next page.)

Primary Examiner—Christine M. Nucker
Attorney, Agent, or Firm—Leydig, Voit & Mayer

[57] ABSTRACT

Methods and procedures are described for the isolation of human progestin receptors and for the use of human progestin receptors as immunogens in producing both monoclonal and polyclonal antibodies. These antibodies are used for the detection of progestin receptors, such as the progesterone receptor both normal and cancerous tissues.

30 Claims, No Drawings

OTHER PUBLICATIONS

Sullivan et al., Isolation of Steroid Receptor Binding Protein from Chicken Oviduct and Production of Monoclonal Antibodies, Biochemistry 24(15):4214–22, 1985.

Coffer et al., Immunoradiometric Studies with Monoclonal Antibody Against a Component Related to Human Estrogen Receptor, Cancer Research 45:3694–98, Aug. 1985.

Jensen et al., Basic Guides to the Mechanism of Estrogen Action, Ben May Laboratory of Cancer Research, The University of Chicago, Chicago, Illinois, pp. 387–414.

DeSombre et al., Correlation of ER-ICA with Quantitative ER Assays and Time to Recurrence and Survival in Breast Cancer, AACR Abstract, AACR Annual Meeting, May 22–25, 1985, Houston, TX.

Grandics et al., A New Affinity Resin for Purification of Non-Transformed Avian Progesterone Receptor, Endocrinology 110(3):1055–57, 1982.

Horwitz et al., In situ Photolinked Nuclear Progesterone Receptors of Human Breast Cancer Cells: Subunit Molecular Weights after Transformation and Translocation, Endocrinology 113(6):2195–2201, 1983.

Gormley et al., A Controlled Pore Glass Bead Assay for the Measurement of Cytoplasmic and Nuclear Glucocorticoid Receptors, J Steroid Biochem. 22(6):693–98, 1985.

Luben et al., Monoclonal Antibodies to Hypothalamic Growth Hormone-Releasing Factor with Picomoles of Antigen, Science 218:887–89, Nov. 26, 1982.

ANTIBODY TO HUMAN PROGESTERONE RECEPTOR AND DIAGNOSTIC MATERIALS AND METHODS

BACKGROUND OF THE INVENTION

1. Field of the Invention

Methods for the isolation of human progesterone or progestin receptor (hPR) from cells and the use of this hPR for antibody production are described. This antibody production includes both polyclonal and monoclonal antibody specific for the human progestin receptor and methods for the detection and measurement of human progestin receptor using the antibodies produced.

2. Background of the Invention

The present invention relates generally to the isolation of the human progesterone or progestin receptor and the use of this receptor protein in the production of antibody molecules. More specifically, this invention provides novel antibody preparations which have specific reactivity with the hPR and provide improved test methods and reagents for the detection and quantification of hPR proteins by means of immunological reactions.

It has been determined that certain tissues, notably certain human breast cancer tissues, are steroid hormone "dependent" in the sense that systemic deprivation of supportive hormones will result in regression of tissue growth and cell proliferation. As one example of this dependence, bilateral adrenalectomny can effect striking remission of advanced breast cancer in postmenopausal women and similar remissions are observed after hypophysectomy. Estrogen deprivation by surgical ablation of tissue responsible for estrogen production and/or endocrine additive therapy afford the most effective treatments presently available for advanced breast cancer. Unfortunately, less than one-half of the premenopausal patients and even a smaller fraction of postmenopausal patients respond to this type of therapy—indicating that breast cancer tissue is not always of the cellular type which is estrogenic hormone dependent. Consequently, it is significant to the prognosis and treatment of human breast cancer to be able to ascertain whether excised tumor tissue of a breast cancer patient is comprised predominantly of estrogen dependent cell types. On the basis of such information, a reasonable ablation response prediction may be made. Surgical removal of estrogen producing glands for the purpose of estrogen deprivation may be restricted to those patients most likely to be helped by the procedure. Correlatively, other breast cancer patients can be spared the trauma of essentially useless surgery and may be placed immediately into alternative therapeutic programs such as radiation or chemotherapy.

Progesterone receptors are specific progesterone binding proteins that are specific for binding progesterone or other progestins and are involved in the stimulation of progesterone specific biological responses in certain tissues. These responsive target tissues are activated by the binding of the progesterone to the progesterone receptor resulting in the progesterone receptor complex becoming tightly bound to the chromatin of the cell, thereby resulting in the ability of the cell to synthesize certain types of RNA. This regulation of gene expression in eukaryotic cells by progestins and other steroid hormones involves interaction of the specific intercellular receptor proteins with both steroid hormone and the genome, resulting in the activation of specific sets of responsive genes (1).

A result of the interaction between a hormone receptor and a steroid hormone is a change in DNA synthesis, RNA synthesis and production of proteins involved in the regulation of cell proliferation, differentiation and physiological function in diverse tissues. The hormone estrogen induces the progesterone receptor protein, whose synthesis appears to be transcriptionally regulated by the binding of estrogen receptor to chromatin. In addition, such steroid hormones and their receptors appear to be involved in the regulation of abnormal growth in various tumors and tumor cell lines (2). Data from several laboratories (3) suggest that steroid hormone action may involve the binding of the hormone directly to an intracellular receptor molecule, which is weakly associated with nuclear components in the absence of the ligand (steroid). Binding of the hormone ligand to its receptor results in the conversion of the steroid-receptor complex to a form which now associates with high affinity to one or more nuclear components. What is known about steroid receptors has come from the use of radiolabeled hormones (4) and hormone analogs to detect, quantify and characterize those intercellular steroid binding receptor proteins principally found in reproductive tissues. Although distinct steroid and DNA-binding domains have been postulated to exist for all steroid receptor proteins, including the progesterone receptor, little data is available on the detailed structure, composition and chemical properties of the subunits which bind both steroid hormones and DNA, and virtually nothing is known about the involvement of other non-steroid-binding components involved in the tissue response to steroid hormones.

Heretofore, the presence of steroid hormone dependent tissue in mammary tumor samples has principally been determined by quantitative detection of steroid hormone receptors in the sample through radiochemical assay. According to one such procedure, radioactive (e.g., tritiated) progesterone is added to the cytosol—or supernatant fraction—of a homogenized tissue sample, and the tritiated progesterone reversibly combines with any hPR protein present in the cytosol. The specimen is then subjected to low-salt, sucrose density gradient ultracentrifugation, and the receptor-progesterone complex, being a large molecule, sediments with a characteristic velocity. A radioactive count can be used to quantify the complex. This procedure is carried out in the presence and in the absence of an inhibitor of the desired specific binding in order to identify and exclude any binding that is non-specific. The above analytical technique requires use of rather sophisticated, costly and uncommon ultracentrifugation apparatus, the operation of which requires a high degree of skill on the part of the laboratory worker. Other methods employed for receptor assays have similar limitations. [See, e.g., Korenman et al., J. Clin. Endocrinol. & Metab. 30, 699–645 (1970)]. As a result, despite the exceptional usefulness of quantitative detection of the hPR in prediction of response to endocrine therapy, the utilization of prior radiochemical assays is limited by scientific, geographic, and economic considerations.

The production of monoclonal antibodies to steroid hormone receptors has recently been reviewed by E. Milgrom in Pharmac Ther., Volume 28, 389 (1985). The production of sensitive immunoassays for human steroid receptor proteins has been described by Nolan et al. in Current Controversies In Breast Cancer, University of Texas Press, 1984. The application of immunochemical techniques to the analysis of estrogen receptor structure and function has been described by G. L. Greene in Biochemical Actions Of Hormones, Volume XI, Chapter 8 (1984). The importance of receptors in the management of breast cancer has been shown by Hawkins in the British Journal Of Hospital Medicine, p. 160, September 1985.

The clinical utility of determining whether a cancer is hormone responsive, has been shown by correlations of patient responses to endocrine therapies with the human estrogen receptor (hER) and the human progesterone receptor (hPR) content of breast cancers. These studies have clearly established the importance and utility of the biochemical hER and hPR assays. While only 25–30% of unselected breast cancer patients obtained objective remission of metastatic disease following various endocrine therapies, more than 75% of the patients whose cancers contained both hER and hPR benefit (5), whereas there is only a 33% response rate if only one of the two steroid receptors is present (6). Moreover, those patients whose primary cancers are hER/hPR-rich are more likely to have a longer disease-free interval than those cancers that lack either receptor (7, 8). Data from several clinical studies (9-11) indicate that the hPR (as an end-product of estrogen action) is an even better marker than the estrogen receptor for favorable prognosis and endocrine responsiveness in breast cancer. Previously the receptor-binding assays in which hER and hPR were measured was by saturational binding of radio-labeled steroid hormones, or their analogs to the appropriate receptor protein. This assay method requires considerable laboratory skill and effort and the availability of immuno-diagnostic procedures would greatly facilitate the determination of the presence of steroid receptors.

It has been recognized that immunochemical techniques for hPR detection would, if available, provide a simpler and less costly analytical procedure and be susceptible to more widespread clinical use. However, the art has heretofore not been provided with any definitive demonstration that antibodies to hPR could be generated and effectively employed in the detection of hPR in human tissue and cells. Indeed, the difficulty in isolating hPR has created doubt that it would ever be successfully developed.

Other steroid receptor antibody-dependent assays have been developed. The generation of well-defined hER antibodies was first reported by Greene et al. (12). Polyclonal antibodies have been raised against partially purified preparations of glucocortoid receptors (13–15), calf and human estrogen receptor (16, 17), and progesterone receptors isolated from rabbit and guinea pig uterus (18, 19), and chick oviduct (20). In addition, autoimmune antibodies to androgen receptor have been found in human serum (21). In some cases antibodies will bind to corresponding receptors from other species. However, all antibodies directed against steroid binding subunits appear to be hormone specific. Monoclonal antibodies have been prepared against estrogen receptors (22–24), the glucocortoid receptor (25–27, 28), and rabbit progesterone receptor (28). The rabbit progesterone receptor antibody was reported to cross-react the hPR but only with a much lower affinity. Monoclonal antibodies have been prepared against pututative non-hormone binding forms of the B-subunit (30) and A-subunit (31) of chicken oviduct PR, although the relationship between these B and A "antigens" and the steroid binding subunits have not been established. Both polyclonal (32) and monoclonal (33) antibodies have been prepared against proteins that appear to be closely associated with steroid receptors, but which themselves will not bind hormones.

SUMMARY OF THE INVENTION

According to the present invention, there is provided for the first time the isolation of human progestin receptors and the use of these isolated progestin receptors to produce immunoglobulins specific for the human progestin receptor. More specifically, immunoglobulins were obtained either from the serum of animals immunized with a purified preparation of the progestin receptor or from monoclonal antibodies produced using the progestin receptor as an immunogen. The immunoglobulins produced in this invention have among their properties the following:

(a) ability to cause the immunoprecipitation of progestin receptor from a fluid;

(b) ability to form immunoglobulin progestin receptor complexes which sediment at a increased velocity;

(c) ability to adsorb progestin receptors from biological extracts; and (d) ability to bind progestin receptor in permeabilized tissue, tumor sections or individual cells.

The immunoglobulins of this invention may be IgA, IgG, IgM, IgD, or IgE, and they may be produced by either monoclonal or polyclonal methods. Another aspect of this invention is the purification of the human progestin receptor to more than 2% of the protein. More preferably, the purified progestin receptor is more than 20% pure, and most preferably is more than 60% pure. Yet another aspect of the present invention comprises the combining of the anti-human progestin receptor with a detectable marker. Yet another example of the present invention is the combination of the human progestin receptor with a carrier such as detectable particles or to a substrate suitable for chromatography. Another example of the present invention is the use of the anti-human progestin receptor immunoglobulin in a diagnostic assay for detecting the presence of human progestin receptor in a biological sample such as human cancer tissue. Still another aspect of the present invention is a method obtaining immunoglobulins specific for human progestin receptor wherein the receptor is used as an immunogen in an animal system or as an immunogen in sensitizing lymphocytes, either invivo or invitro (42). Still another method of the present invention is the production of monoclonal antibodies by the formation of hybridoma cell lines using sensitized lymphocytes. Another aspect of the present invention is a histological method of determining the progesterone receptor in a tissue, cell, or biological fluid wherein human progesterone receptor specific antibody bearing a detectable marker contacts and identifies the progesterone receptor. A final object of the present invention is the preparation of diagnostic kits useful for the detection of human progesterone receptor, the kits containing antibody to the human progesterone receptor in combination with detectable markers and optionally with suitable carrier solutions. Further aspects and advantages of the invention will become apparent to those skilled in the art upon consideration of the following description of the specific embodiments of the invention.

DESCRIPTION OF THE SPECIFIC EMBODIMENTS

Despite the value of current hER and hPR assays, there is a need to improve the accuracy of response and prognosis predictions for breast cancer and other gynecologic cancers. The favorable correlations observed between biochemical hER assays and quantitative and cytochemical immunoassays for hER in more than 500 breast cancers (34-36) indicate the potential value of immunochemical approaches to steroid receptor analysis in endocrine-responsive cancers. Because hPR is also an important prognostic and diagnostic tumor marker, it is clear that a means for locating measuring and purifying hPR that does not depend on the binding of radiolabeled hormone would extend our knowledge of receptor-mediated events and hormone responsiveness in certain cancers. The use of monoclonal antibodies to hPR is an excellent method for determining the location specificity and affinity of hPR proteins both in the presence and in the absence of progestin hormones. In addition, specific antibodies are readily immobilized to aid in the purification and quantitation of receptor protein. They are tagged with indicator enzymes, electron opaque substances or, radioisotopes, to localize and/or quantify their receptor in tissues, cultured cells or cell-free extracts. The immunochemical assays for hPR are comparatively simple, rapid, sensitive and specific, easily standardized, less affected by receptor alteration during manipulations, and they are capable of measuring total steroid occupied and unoccupied receptor present in the sample. In addition, an immunocytochemical assay provides information about the disproportional distribution of hPR-containing cells in a tumor as well as in the surrounding normal tissue. Such information is important in determining the presence of a subpopulation of hormone insensitive tumor cells in a population of responsive tumor cells. Simultaneous evaluation of hER and hPR in tumors by similar methodologies permits an assessment of both parameters as complementary indicators of the tumor status and responsiveness to various therapy procedures. Such dual testing saves time, effort and the maintenance of two types of receptor assay procedures in the diagnostic laboratory.

Other uses for the progesterone receptor antibodies include the detection and quantification of the location of progesterone receptor in intracellular locations, in solutions and in specific tissues. Such antibodies are also useful for distinguishing nonprogesterone receptor containing tissue from human progesterone receptor containing tissue. Human progesterone receptor specific antibody may be used to determine the presence of hPR in blood or other bodily fluids. Such determinations are useful in evaluating whether hPR containing cells have been damaged or are dying. Progesterone receptor antibody may be also used to quantitate the amount of hPR in uterine tissue during surgery or during a dialation and cuitage (D & C). An additional use of hPR antibody is in the area of drug design. The hPR antibody and progesterone receptor isolated through the use of such specific antibody are useful in the design of progestin agonist or antagonist by evaluating binding affinities.

The production of specific hPR polyclonal and monoclonal antibodies required the isolation and purification of the hPR. Once purified, or partially purified, the hPR was used in the production of polyclonal or monoclonal antibodies.

These antibodies may be produced in any animal with a competent immune system capable of responding to the hPR or hPR complex containing bound progesterone. Among the preferred species of animals are mammals such as rabbit, rat, mouse, goat, sheep, horse, cow, or pig. Among the antibody classes are all immunoglobulin types including but not limited to IgG, IgA, IgM, IgD, and IgE. The entire anitbody need not be used, but rather only fragments, such as Fab, (Fab$^1$)$_2$, Fv or the like. The critical factor is the affinity of the antibody fragment for the hPR.

The progesterone receptor itself has a sedimentation of 4S in hypernic solution and 8-10S in hypotonic solution. When used as an immunogen, the progesterone receptor may be in either a native state or a denatured state. Denaturation may be due to heat, pH, or chemical denaturation using organic solvents. The progesterone receptor may be complexed with progesterone or progesterone analogs when used as an immunogen. In addition, the progesterone receptor may be phosphorylated or unphosphorylated.

Antibodies to hPR are specific for binding to the intercellular progestin-binding receptor proteins from human tissues, cancers and cultured tumor or non-tumor cell lines. These hPR specific antibodies are found in the serum of animals immunized with hPR or obtained from hybrid cells resulting from the fusion of splenic lymphocytes from animals and fused with myelomal cells or of from invitro transformed lymphocytes. Monoclonal antibodies may be obtained from mammalian lyphocytes which have been transformed by viral particles, mutagens or other transforming agents. Any myeloma cell may be used in the production of hybrid cells producing hPR antibody, but most preferably the SP2/0-Ag14 or X63-Ag8 (ATCC Numbers CRL-1581 and CRL-1580 respectfully) myelomas cell lines.

Both polyclonal and monoclonal antibodies have the following properties: The ability to specifically bind to epitopes present on specific progestin receptors in human tissues, tumors and their extracts, as determined by (a) immunoprecipitation of progesterone receptor in a fluid upon addition of antibodies and one or more reagents such as heterologous antibodies directed against the first immunoglobulin, capable of salting out the antibody receptor complex; (b) the ability to form a complex with hPR which has an altered sedimentation rate when analyzed by ultracentrifugation, and altered elution characteristics when analyzed by gel filtration or steric exclusion chromatography; (c) the ability to adsorb hPR from cell extracts or other fluids when bound to an insoluble support or surface, or when antibody receptor complex is adsorbed to an insoluble support which is combined with antibody such as *S. Aureus* protein A linked to a matrix or surface; (d) the ability to bind to hPR in permeabilized tissue, tumor sections or individual cells.

Any of the antibodies described above may be combined with a detectable marker substance such as a radioisotope or a colorimetric reagent (chromogen), and electron-opaque material (colloidal gold), or other immunochemically active or inert substance which provides a means of detecting or measuring the presence or amount of antibody receptor complex formed. The hPR itself may be labeled with a marker substance, including synthetic or natural progestins such as progesterone (4-pregnen-3, 20-dione), promegesterone 17, 21-dimethyl-19-norpregn-4, 9-diene-3, 20-dione, (R5020); 16 alpha-ethyl-21-hydroxy-19-norpregn-4-ene-3, 20-dione; ORG2058; other progestins such as etisterone, medroxyprogesterone acetate, hydroxyprogesterone caproate, norethindrone, nurethynodrel, ethynodiol diacetate, dydrogesterone, dimethisterone, ethinylestrenol, megestrol acetate or norgestrel or progesterone antagonists.

According to the invention, novel immunological reagents are provided when the immunoglobulin fraction of serum of an animal immunized with purified hPR-progestin complex or from similiar hybridoma cell lines are employed, with or without prior treatment to remove non-specific antibodies or other proteins in the immunoglobulin. These immunoglobulins are used to sensitize immunologically inert particulate materials such as stabilized immunologically inert particulate materials such as stabilized erythrocytes (e.g., prepared according to the procedures of U.S. Pat. Nos. 3,714,345; 3,715,427; and/or 3,924,541), bentonite, collodium, crystalline cholesterol, quartz, synthetic resins, various kinds of synthetic latex (see, e.g., U.S. Pat. No. 3,551,555) polystyrene beads, or liposomes prepared from phospholipids and sterols including radioactive material-containing or free radical-containing liposomes. Such sensitized particles are useful when employed in direct agglutination assays wherein hPR in a tissue sample will be bound to and effect agglutination of the particles, allowing quantification of the complex by standard immunoassay techniques. Alternatively, when antibody materials are employed to sensitize radioactive material or free radical-containing particles, hPR content of a tissue sample homogenizate may be determined by adding such particles to the sample, withdrawing particles as aggregated. Further, techniques using radiochemically-labelled, or enzyme-linked, or otherwise detectable anti-hPR immunoglobulins may provide the basis for hPR assays that detect the hPR. Substantial advantages are expected to accompany procedures which are independent of the reversible binding of progestins in the sample to hPR. In particular, such procedures should be able to detect the amount of free hPR as well as hPR already associated with non-radioactive, endogenous progestins.

In one further application, anti-hPR provides the basis for a specific immunohistochemical procedure for the detection and quantification of hPR in pathologic sections of cancer tissue. Such sections are incubated with solutions of the antibody and, after washing with buffer, incubated either with a flurorescent-labelled second antibody (to the immunoglobulin) or with peroxidase-antiperoxidase-complexed second antibody. After further washing, the sections are examined for the presence of hPR by fluorescent microscopy, or after peroxidase staining, by light microscopy. This technique allows the detection of hPR in tissue sections carried out in the same surgical pathological laboratory where the cancer diagnosis is made.

Furthermore, since tumor components or their partial degradation components are often released into the blood, an assay for immunoreactive fragments or hPR in the sera of patients with (or suspected of having) an hPR containing cancer could provide a means for early diagnosis of metastatic disease.

Definitions

Biological Sample: Any organ, tissue, tumor, cell or extract of any organ, tissue, tumor or cell or any body fluid or portion of any body fluid.

Cancer: Any malignant, hyperplastic, neoplastic, pre-cancerous or histologically abnormal cell or tissue.

Chromatography: Either affinity, size exclusion, hydrophobic or ion exchange chromatography.

Detectible Markers: Any radioistopes such as $^3$H, $^{125}$I, $^{131}$I; any fluorescers such as fluorescein, phycobiliproteins, rare earth chelates, dansyl, rhodamine; enzyme substrates and inhibitors, enzymes such as horseradish peroxidase, glucose oxidase, glucose-6-phosphate dehydrogenase, acetylcholinesterase etc.; particle such as dextran, sepharose beads, polystyrene beads, agarose, metal particles, a magnetic particles and the like.

Monoclonal: A system employing immunoglobulin producing cells derived from a single cloned cell and producing antibody of a single type, often the result of cell fusion such as hybridoma cell lines.

Polyclonal: A system producing immunoglobulins derived from many cell types generally with multiple affinities for the immunogen, generally referring to the immunoglobulins produced invivo in an animal following immunization.

Progestin Receptor: The receptor normally bound by progesterone but which is capable of binding any progestin. Receptor may be composed of the A polypeptide, the B polypeptide or a mixture of the A and B polypeptide forms.

Releasate: Any medium containing proteins released by a cell or tissue.

Transforming Agent: Any chemical mutagen, any form of radiation causing mutation, any virus or any procedure of culturing cells that results in the production of immortal cell lines.

The following Examples are offered by way of illustration and not by way of limitation.

Example I.—Purification of the antigen

The cytosol and nuclear forms of hPR from T47D human breast cancer cells (ATCC deposit no. HTB, 133) were partially purified by selective adsorption to Sterogel (37), a commercial preparation of deoxycorticosterone coupled to Sepharose 2B, and by adsorption to a monclonal antibody (JU601) coupled to Sepharose 4B. The hPR complex consists of two dissimilar subunits that can be photoaffinity labeled specifically with the synthetic progestin $^3$H-R5020 and visualized on autoadiograms of reducing SDS gels at $M_r$ 95,000 (A subunit) and at $M_r$ 120,000 (B subunit) (38). These two proteins may represent different gene products or A may be derived from B. Cytosol was prepared by homogenization of cells in four volumes of 50 mM potassium phosphate buffer, pH 7, containing 10 mM sodium molybdate and 10 mM thioglycerol (buffer A), and nuclear extract by extraction of the nuclear pellet with buffer A containing 0.4 M potassium chloride. Human progesterone receptor content was routinely analyzed by specific adsorption of receptor labeled with $^3$H-ORG 2058 (ORG*), or $^3$H-R5020, to Controlled Pore glass beads (39,40), analagous to estrogen receptor assays. The validity of the method was verified by comparison with standard sucrose density gradient and dextran-coated charcoal analyses for hPR. In a typical purification (Table I), 176 ml of cytosol containing 9700 pmol of hPR was passed through a 10-ml column overnight at 4° C.; under these conditions, 90% of the available receptor bound to the adsorbent. After washing with loading buffer, bound receptor was eluted batchwise with buffer A containing 10% glycerol (buffer B), 10% dimethylformamide and $1 \times 10^{-5}$ M ORG* (4.5 Ci/mmol). In some cases, unlabeled progesterone was used to elute hPR. Eluted steroid-receptor complex was then chromatographed on DEAE-Biogel and eluted stepwise with buffer B containing 0.2 M NaCl. Bound progesterone can be readily exchanged by incubation of steroid-receptor complex with ORG* or $^3$H-R5020 in buffer B for 5 hr. at 4° C. Unoccupied nuclear hPR was purified in the same manner, except that the loading buffer contained 0.4 M KCl. The yield of receptor (both subunits) after the two-step purification was in the range of 30-70% and the purity was 2-15% of the specific radioactivity expected for an average molecular weight of 100,000 daltons. Like the crude hPR, purified hPR photoaffinity-labeled with $^3$H-R5020 migrated as two bands at 120 kDa (B) and 95 kDa (A).

TABLE 1

PURIFICATION OF T47D CYTOSOL HUMAN PROGESTERONE RECEPTOR

| Fraction | Protein (mg) | Total hPR* (nmol) | Specific activity (pmol/mg) | Yield (%) | Purity° (%) | Purif. factor |
|---|---|---|---|---|---|---|
| 1. Cytosol | 405 | 9.68 | 24 | — | 0.2 | 1 |
| 2. Sterogel elute | — | 6.18 | — | 64 | — | — |
| 3. DEAE elute | 5.48 | 4.82 | 880 | 50 | 8.8 | 37 |

*Determined by specific binding to Controlled-Pore glass beads.
°Assuming one ORG* bound to a protein of $M_r$ 100,000 (approximate average of 120K and 95K [$^3$H]R5020-hPR bands on SDS gels).

Example II—Preparation and characterization of polycolonal hPR antibodies

Animals were immunized by subcutaneous injection of T47D steroid-receptor complex, eluted from DEAF Biogel (2-15% pure) or from the JU601 immunoadsorbent (20-60% pure), emulsified in Freunds complete or incomplete adjuvant. Three male Lewis rats (K, W) and one Balb/C mouse responded, producing detectable antibody to hPR at serum dilutions of >1:800 after primary injections of 300-500 pmol of steroid-receptor complex in complete adjuvant followed by 2-4 booster injections of 150-500 pmol of receptor in incomplete adjuvant. The animals differed in that one (rat K) was injected with receptor which was denatured by heating with 1% SDS prior to emulsification in adjuvant. The formation of immune complexes between hPR and polyclonal antibodies partially purified by ammonium sulfate fractionation of rat serum was demonstrated by (1) an increase in the sedimentation rate of ORG*-, $^3$H-R5020-, or $^3$H-progesterone-receptor complex in sucrose gradients, (2) by specific precipitation of the same complexes when goat antibody to rat IgG was added to a mixture of rat antiserum and labeled hPR, and (3) by the appearance of antibody-receptor complexes in the void volume of a TSK4000 steric exclusion column eluate after high pressure liquid chromatography. The broadness of the immune complex peak observed on sucrose gradients indicated the presence of multiple antibody idiotypes, each recognizing a different region of the receptor molecule. The virtually complete reaction of antibody (s) with receptor indicated that these antibodies recognized both progestin-binding species (B and A).

Example III—Preparation of monoclonal antibodies

Fourteen monclonal antibodies, including 10 derived from two Lewis rats and 4 from a Balb/C mouse, were prepared against the A or B steroid-binding components of the human (T47D) progesterone receptor. The known characteristics of these antibodies are summarized in Table 2. Splenic lymphocytes were fused with the X63-Ag8.653 mouse myeloma (41), a nonsecreting variant of the P3-X63-Ag8 cell line. Antibody-producing hybridomas were detected by specific precipitation of labeled hPR in the presence of hybridoma medium, normal rat serum carrier and goat antibody to rat immunoglobulins. Assays were carried out in 96-well microtiter plates. All hybridomas have been cloned by limiting dilution and expanded in roller bottles or as ascites tumors in athymic mice. Antibodies are purified by immunoadsorption to a column of goat antibody to rat IgG, conjugated to Sepharose 4B, followed by gel filtration through Biogel A-1.5 m for IgMs. On reducing SDS gels, the purified antibodies migrate as two bands: 70 kDa (mu chain) and 23 kDa (kappa chain) for IgMs, and 50 kDa (gamma chain) and 23 kDa (kappa) for IgGs.

Characterization of monoclonal antibodies to hPR

Of the 14 antibodies listed in Table 2, 13 recognized epitopes shared by the A and B components, as judged by immunoblot analysis of T47D and MCF-7 cytosol and nuclear extracts after SDS gel electrophoresis, and by sucrose gradient analysis of their interaction with $^3$H-ORG 2058-hPR. One antibody, KC 146, was specific for the B component. Like the hER monoclonal antibodies, the hPR antibodies had high affinity for steroid-occupied as well as unoccupied receptor and recognized both nuclear and cytosol forms. Three of the antibodies cross-reacted with the A and B components of rabbit progesterone receptor, and one of these (JZ B39) recognized rat and calf uterine progesterone receptor as well. However, the mouse monoclonal antibody which is specific for human B (KC 146) also recognized the B component of PR in cytosols from rat and calf uterus and chicken oviduct. None of these antibodies reacted with MCF-7 $^3$H-estradiol-receptor complex in salt-containing gradients. Although 12 of the 14 antibodies appeared to be specific for hPR A and/or B components on immunoblots of T47D and MCF-7 extracts after SDS gel electrophoresis, two (JU145 and JU601) recognized at least one other protein on these blots. When T47D progesterone receptor present in either cytosol or nuclear extracts was photoaffinity-labeled with $^3$H-R5020 and immunopurified on an adsorbent consisting of JU601 IgM conjugated to CNBr-activated Sepharose 4B, the SDS-eluted proteins migrated as two radioactive bands on reducing SDS gels, at 120 kDA and 95 kDa; the 95 kDa band was dominant. The same bands were present in silver-stained gels, along with three or four minor bands (non-radioactive) of lower molecular weight.

TABLE 2

CROSS REACTIVITY OF MONOCLONAL ANTIBODIES TO HUMAN PROGESTERONE RECEPTOR

| ANTIBODY | ISOTYPE | SOURCE OF PROGESTERONE RECEPTOR | | | | |
|---|---|---|---|---|---|---|
| | | BREAST CANCER T47D | UTERUS | | | OVIDUCT CHICKEN |
| | | | CALF | RABBIT | RAT | |
| JU 601 | IgM | + | − | + | − | − |
| JU 145 | IgM | + | − | − | − | − |
| JZB39 | IgM/IgG$_{2a}$ | + | + | + | + | − |
| JZB63 | IgM | + | − | − | − | − |
| KC 34 | IgG$_1$ | + | − | − | − | − |
| KC 75 | IgG$_1$ | + | − | + | − | − |
| KC 102 | IgG$_1$ | + | − | − | − | − |
| KC 146 | IgG$_1$ | + | + | + | + | + |
| KD 38 | IgG$_1$/IgG$_{2a}$ | + | − | − | − | − |
| KD 42 | IgG$_{2a}$ | + | − | − | − | − |
| KD 67 | IgG$_{2a}$ | + | | | | |
| KD 68 | IgG$_{2a}$ | + | | | | − |
| KD 81 | IgG$_{2a}$ | + | | | | − |
| KD 83 | IgG$_{2a}$ | + | | | | − |

Example IV—Development and application of hPR immunoassays

For quantitative measurement of hPR in cell extracts and fluids, an enzyme immunoassay similar to the one developed for hER enzyme immuno assay (hER-EIA) was developed for analysis of extracts of hormone-responsive cancers. Several combinations of the antibodies listed in Table 1 were tested on polystyrene beads and at least one combination (KD 68/JBZ 39) appeared to have the necessary sensitivity and specificity for accurate hPR measurement. A prototype assay, in which polystyrene beads were coated with KD 68 and JZ B39 was conjugated to horse radish peroxidase, was used to evaluate the hPR content in cytosols (0.2 ml) from 28 human breast tumors. The same cytosols were analyzed by the NEN Progesterone Receptor Assay kit, which relies on Scatchard analysis of steroid binding to hPR. A comparison of the results obtained by the two methods yielded a correlation coefficient of 0.96. The sensitivity of the hPR-EIA was 2–3 fmol hPR/ml. Thus, the hPR-EIA analysis correlated well with conventional steroid binding results for hPR in breast tumor extracts. In addition, the sensitivity of the hPR-EIA was comparable to hER-EIA and to conventional hPR assay methods.

To assess the feasibility of establishing an indirect immunoperoxidase method for localizing hPR in hormone-responsive tissues and cancers, analagous to the human estrogen receptor immunocytochemical assay (hER-ICA), the JZB39 antibody was used to localize immunoreactive hPR in frozen sections of various human tissues and tumors, as well as in fixed MCF-7, T47D and MDA-MB-231 cells. Tissue sections (8/m) or cells were fixed in picric acid-paraformaldehyde, blocked with 10% normal goat serum and incubated with JZB 39 IgG (10 g/ml) in PBS containing 10% goat serum for 30 min at room temperature. All other steps were the same as those established for ER (8,9). Each specimen was analyzed for immunoreactive ER with monoclonal H222 IgG. As observed for estrogen receptor, specific staining for hPR was confined to the nuclei of all stained cells, regardless of hormone status, and the proportion of stained tumor cells varied considerably from specimen to specimen. Staining was absent in non-target tissues, such as colon epithelium, hPR-poor breast cancers and non-estrogen treated MCF-7 cells; in addition, specific staining was abolished by the addition of partially purified hPR to primary antibody. Little or no cytoplasmic staining for hPR or hER has been observed in any of the tissues or tumor cells examined thus far. Although the JZB 39 IgG has proved most useful thus far for hPR localization, the KD 67 and KD 68 antibodies could work as well or better. A summary of specificity and staining characteristics for all 14 available antibodies is shown in Table 3. Only the JU 145 and JU 601 IgMs lack the necessary specificity for hPR. The mouse antibodies and JZB63 lack the sensitivity needed, but are specific for hPR. In a preliminary evaluation of 50 breast tumors by hPR-ICA, a statistically significant relationship was observed between the cytosol hPR content, as determined by a steroid-binding assay, and the presence or absence of specific staining for hPR in tumor cells. In all cases where there was disagreement, immunoreactive receptor was detected when biochemical values were low. While the exact sensitivity of the immunocytochemical assay for hPR has not been determined, these results indicate that hPR localization with specific monoclonal antibodies is feasible.

The JZB 39 antibody also has use as a probe for hPR in breast tumors, especially in comparison to biochemically determined nPR in cytosols and to hER measurement and localization with the hER-ICA method.

TABLE 3

IMMUNOCYTOCHEMICAL STAINING WITH MONOCLONAL HUMAN PROGESTERONE RECEPTOR ANTIBODIES

| Monclonal Antibody | Species, Isotype | Intensity of Staining in Selected Tissues | | | |
|---|---|---|---|---|---|
| | | hPR-rich[1] Breast Ca | hPR-poor[2] Breast Ca | Human Endometrium[3] | Human Colon |
| JU601 | rat, IgM | +++ | +++ | ++++ | +++ |
| JU145 | rat, IgM | ++ | +++ | +++ | ++ |
| JZB63 | rat, IgM | ++ | − | ++ | − |
| JZB39 | rat, IgG$_{2a}$ | ++++ | − | ++++ | − |
| KD38 | rat, IgG$_{1a}$ | +++ | − | +++ | − |
| KD42 | rat, IgG$_{2a}$ | +++ | − | ++ | − |

TABLE 3-continued

IMMUNOCYTOCHEMICAL STAINING WITH MONOCLONAL HUMAN PROGESTERONE RECEPTOR ANTIBODIES

| Monclonal Antibody | Species, Isotype | Intensity of Staining in Selected Tissues | | | |
|---|---|---|---|---|---|
| | | hPR-rich[1] Breast Ca | hPR-poor[2] Breast Ca | Human Endometrium[3] | Human Colon |
| KD67 | rat, IgG$_{2a}$ | ++++ | − | ++++ | − |
| KD68 | rat, IgG$_{2a}$ | ++++ | − | ++++ | − |
| KD81 | rat, IgG$_{2a}$ | +++ | − | ++ | − |
| KD83 | rat, IgG$_{2a}$ | +++ | − | +++ | − |
| KC34 | mouse, IgG$_1$ | + | − | + | − |
| KC75 | mouse, IgG$_1$ | ++ | − | ++ | − |
| KC102 | mouse, IgG$_1$ | + | − | + | − |
| KC146 | mouse, IgG$_1$ | + | − | + | − |

[1]Human progesteron receptor content greater than 1000 fmol/mg cytosol protein by DCC analysis.
[2]Human progesterone receptor content less than 5 fmol/mg cytosol protein by DCC assay.
[3]Proliferative phase endometrium.

References Cited

1. G. M. Ringold, *A. Rev. Pharmac. Tox.* 25, 529, (1985); J. N. Anderson, in *Biological Regulation and Development*, R. F. Goldberger and K. R. Yamamoto, Eds. (Plenum, New York, 1985), vol. 3B, p. 169; B. S. Katzenellenbogen, *Annu. Rev. Physiol.* 42, 17 (1980); J. Gorski and F. Gannon, *Annu. Rev. Physiol.* 38, 425 (1976); C. W. Bardin, L. P. Bullock, N. C. Mills, Y.-C. Lin and S. Jacobs, in *Receptors and Hormone Action*, B. W. O'Malley and L. Birnbaumer, Eds. (Academic, New York, 1978), vol. 2, p. 83; J. D. Baxter and P. H. Forsham, *Am. J. Med.* 53, 573 (1972); E. V. Jensen et al., *Proc. Natl. Acad. Sci. U.S.A.* 59, 632 (1968); K. R. Yamamoto and B. M. Alberts, *Annu. Rev. Biochem.* 45, 721 (1976); M. R. Sherman and J. Stevens, *Annu. Rev. Physiol.* 46, 83 (1984).

2. M. Lippman in *Breast Cancer: Trends in Research and Treatment* (Raven New York, 1975); M. E. Lippmann and G. Bolan, *Nature* 256, 592 (1975).

3. P. J. Sheridan, J. M. Buchanan, V. C. Anselmo, P. M. Martin, *Nature* 282, 579 (1979); W. V. Welshons, M. E. Lieberman, J. Gorski, *Nature* 307, 747 (1984); W. J. King and G. L. Greene, *Nature* 307, 745 (1984); M. F. Press, N. A. Nousek-Goebel, G. L. Greene, *J. Histochem. Cytochem.* 33, 915 (1985).

4. E. V. Jensen and H. I. Jacobson. Recent Prog. Hormone Res. 18, 387–414 (1962).

5. E. R. DeSombre. P. P. Carbone, E. V. Jensen, W. L. McGuired, S. A. Wells, J. L. Wittliff and M. B. Lipsett. New Engl. J. med. 301, 1011 (1979).

6. E. R. DeSombre. Clinics in Oncol. 1, 191 (1982).

7. S. Saez, C. Chouvet, M. Mayer and F. Cheix. Proc. AACR and ASCO 21, 139 (1980).

8. C. K. Osbourne, M. G. Yochmowitz, W. A. Knight and W. L. McGuire. Cancer Res. 46, 2884 (1980).

9. A. Bertuzzi, P. Vezzoni and E. Ronchi. Proc. AACR and ASCO 22, 447 (1980).

10. M. F. Pichon, C. Pallud, M. Brunet and E. Milgrom. Cancer Res. 40, 3357 (1980).

11. G. M. Clark, W. L. McGuire, C. A. Hubay, O. H. Pearson and J. S. Marshall. New Engl. J. Med. 309, 1343 (1983).

12. G. L. Greene, L. E. Closs, H. Fleming, E. R. DeSombre and E. V. Jensen. Proc. Natl. Acad. Sci. USA 74, 3681–3685 (1977).

13. S. Okret, J. Carlstedt-Duke, O. Wrange, K. Carlstrom and J. A. Gustafsson. Biochem. Biophys. Acta. 677, 205 (1981).

14. H. J. Eisen. Proc. Natl. Acad. Sci. USA 77, 3893 (1980).

15. M. V. Govindan. J. Steroid Biochem. 11, 323 (1979).

16. C. Radanyi, G. Redeuilh, E. Eigenmann, M. C. Lebeau, N. Massol, C. Secco, E. E. Baulieu and H. Richard-Foy. C.R. Acad. Sci. Paris Ser. D. 288, 255–258 (1979).

17. A. I. Coffer, R. J. B. King and A. J. Brockas. Biochem. Internat. 1, 126–132 (1980).

18. F. Logeat, T. V. Mai and E. Milgrom. Proc. Natl. Acad. Sci. USA 78, 1426 (1981).

19. P. D. Feil. Endocrinology 112, 396 (1983).

20. J. M. Renoir, C. Radanyi, C. R. Yang, E. E. Baulieu. Eur J. Biochem. 127, 81 (1982).

21. S. Liao, D. Witte. P.N.A.S. 82, p.8345–8348 (1985).

22. G. L. Greene, C. Nolan, J. P. Engler and E. V. Jensen. Proc. Natl. Acad. Sci. USA 77, 5115–5119 (1980).

23. B. Moncharmont, J. L. Su and I. Parikh. Biochemistry 21, 6916 (1982).

24. G. L. Greene, F. W. Fitch and E. V. Jensen. Proc. Natl. Acad. Sci. USA 77, 157–161 (1980).

25. P. Grandics, D. L. Gasser and G. Litwack. Endocrinology 111, 1731 (1982).

26. H. M. Westphal, C. Moldenhauer and M. Beato. EMBO J. 1, 1467 (1982).

27. S. Okret, A. C. Wikstrom, O. Wrange, B. Andersson and J. A. Gustafsson. Proc. Natl. Acad. Sci. 81, 1609 (1984).

28. F. Logeat, M. T. Vultai, A. Fournier, P. Legrain, G. Buttin and E. Milgrom. Proc. Natl. Acad. Sci. 80, 6456 (1983).

29. E. A. Pierce et al., P.N.A.S. 82 p.8429–8433 (1985).

30. D. P. Edwards, N. L. Weigel, W. T. Schrader, B. W. O'Malley and W. L. McGuire. Biochemistry 1984 23, 4427–4435 91984).

31. A. P. McHale, W. T. Schrader and B. W. O'Malley. Proc. of 7th Inter. Cong. of Endo. Quebec p.1059 (1985), Pub. Excerpta Media, Amsterd.

32. C. Radanyi et al., P.N.A.S. 80, p.1854–2858 (1983). D. A. Sullivan et al. Biochemistry 24 4215–4222 (1985).

33. A. I. Coffer et al., Cancer Research 45, 3686–3693, (1985).

34. W. J. King, E. R. DeSombre, E. V. Jensen and G. L. Greene. Cancer Res. 45, 293–304 (1985).

35. E. R. DeSombre, S. M. Thorpe, C. Rose and W. J. King. Abstract, AACR Meeting, Houston, Texas, 1985.

36. Symposium on Estrogen Receptor Determination with Monoclonal Antibodies. Unpublished results presented in Monte Carlo, December 14, 1984.

37. P. Grandics, R. K. Puri and D. O. Toft. Endocrinology 110, 1055 (1982).

38. K. B. Horwitz and P. S. Alexander. Endocrinology 113, 2195–2201 (1983).

39. V. D. Hospelhorn, T. Shida, E. R. DeSombre and E. V. Jensen. Abstracts 60th Meeting The Endocrine Society, Miami, 1978, p.335.

40. J. A. Holt, M. A. Lorinez and V. D. Hospelhorn. Abstracts 63rd Meeting The Endocrine Society, Cinncinnati, Ohio, p.125.

41. J. F. Kearney, A. Radbruch, B. Liesegang and K. Rajewsky. J. Immunol. 123, 1548–1550 (1979).

42. R. A. Luben, P. Brazeau, P. Bohleln and R. R. Guillemin, Science Vol. 218, p.887–889 (1982).

I claim:

1. An immunoglobulin specific for human progestin receptor comprising an immunoglobulin produced in any animal system in response to an immunogen containing human progestin receptor.

2. An immunoglobulin of claim 1 having the following properties:
   (a) ability to cause the immunoprecipitation of said progestin receptor in a fluid upon addition of said immunoglobulin;
   (b) ability to form an immunoglobulin progestin receptor complex which has a higher sedimentation rate and altered gel filtration chromatography profile compared to the said progestin receptor complex alone;
   (c) ability to adsorb said progestin receptor from cell extracts or other fluids when said immunoglobulin is bound to an insoluble support;
   (d) ability to bind to said progestin receptor in permeabilized tissue, tumor sections or individual cells.

3. The immunoglobulin of claim 1 wherein said immunoglobulin is selected from the following immunoglobulin types: IgA, IgG, IgM, IgD or IgE.

4. The immunoglobulin of claim 1 wherein said animal system is polyclonal.

5. The immunoglobulin of claim 1 wherein said animal system is monoclonal.

6. The immunoglobulin of claim 1 wherein said immunogen is human progestin receptor more than 2% pure.

7. The immunoglobulin of claim 6 wherein said immunogen is human progestin receptor more than 20% pure.

8. The immunoglobulin of claim 8 wherein said immunogen is human progestin receptor more than 60% pure.

9. An immunological reagent comprising the human progestin receptor immunoglobulin of claim 1 covalently or noncovalently attached to a detectible marker.

10. The reagent of claim 9 wherein said detectible marker is a radioisotope.

11. The reagent of claim 9 wherein said detectible marker is an enzyme.

12. The reagent of claim 9 wherein said detectible marker is a fluorescer.

13. The reagent of claim 9 wherein said detectible marker is an electron opaque substance.

14. The reagent of claim 10 wherein said noncavalently attached radioisotope is convalently attached to a progestin or progestin antagonist.

15. An immunological reagent comprising said antiprogestin receptor immunoglobulin of claim 1 is physically attached to a carrier.

16. The immunological reagent of claim 15 wherein said carrier is detectible particles.

17. The immunological reagent of claim 15 wherein said carrier is a water-permeable substance suitable for chromatography.

18. The immunological reagent of claim 15 wherein said carrier is a test device suitable for contacting with a solution containing human progestin receptors.

19. The immunological reagent of claim 15 wherein said carrier is a soluble polymer which can be made insoluble under conditions which do not inactivate said immunoglobulin.

20. An immunological assay for human progestin receptor in a biological sample said assay comprising contacting said sample with the reagent of claim 9 and detecting said detactable marker.

21. An immunological assay according to claim 20 wherein said biological sample is human cancer tissue.

22. A method for isolating human tissue progestin receptors comprising the steps of:
   (a) preparing a soluble medium containing human cell lysate or releasate;
   (b) contacting said soluble medium with the immunoglobulin of claim 1 to form an immunoglobulin-progestin receptor complex; and
   (c) separating said complex from said soluble medium.

23. A method for obtaining immunoglobulins specific for human progestin receptor, said method comprising the steps of:
   (a) preparing a purified progestin/receptor complex of radiolabelled progestin and human progestin receptor by contacting human progestin receptor with radiolabelled progestin and isolating said complex by precipitation, gel filtration, electrophoresis or chromatography;
   (b) inoculating an immunologically competent animal with said progestin/receptor complex and, detecting serum immunoglobulin specific for human progestin receptor from said animal.

24. The method of claim 23 wherein the said immunoglobulins specific for human progestin receptor are produced by the formation of hybridoma cells, said method further comprising the steps of
   (c) isolating sensitized lymphocytes removed from the immune system of said incoulated animal;
   (d) fusing said lymphocytes with myeloma cells;
   (e) selecting hybridoma cells capable of producing immunoglobulins specific for human progestin receptors; and
   (f) isolating said immunoglobulins from said hybridoma cells and hybridoma cell growth media.

25. The method of claim 23 further comprising in place of inoculating said competent animal the steps of:
   contacting said isolated complex with lymphocytes to produce sensitized lymphocytes; and
   (a) fusing said sensitized lymphocytes with myeloma cells to produce hybridoma cells or;
   (b) transforming said sensitized lymphocytes to produce immunoglobulins without fusion;
   isolating immunoglobulins from said hybridoma cells or said transformed cells or from said hybridoma cells or transformed cells growth medium.

26. The method of claim 23 wherein said complex containing progesterone receptor is denatured prior to inoculating said immunologically competent animal.

27. The method of claim 22 wherein said immunoglobulin is bound to a water-permeable substance suitable for chromatography.

28. A method for determining the presence of progesterone receptor in a tissue or cell or body fluids comprising the steps of:
  contacting the antibody of claim 9 with said tissue, cell, or body fluid and,
  detecting said marker.

29. The method of claim 28 wherein said tissue or cell is cancerous.

30. Diagnostic kits for the immunocytochemical detection of human progesterone receptor comprising immunoglobulin specific for human progesterone receptor having a detactable marker attached thereto and a carrier solution suitable for contacting said immunglobulin with human tissue containing human progesterone receptor.

* * * * *

UNITED STATES PATENT AND TRADEMARK OFFICE
CERTIFICATE OF CORRECTION

PATENT NO. : 4,742,000

DATED : May 3, 1988

INVENTOR(S) : Geoffrey L. Greene

It is certified that error appears in the above-identified patent and that said Letters Patent is hereby corrected as shown below:

Column 1, line 31, delete "adrenalectomny" and insert -- adrenalectomy --;

Column 5, lines 59-60, delete "dialation and cuitage" and insert -- dilation and curettage --;

Column 6, line 31, delete "myelomal" and insert -- myeloma --; line 31, delete "of"; line 33, delete "lyphocytes" and insert -- lymphocytes --; line 38, delete "myelomas" and insert -- myeloma --; line 52, delete "chromotography" and insert -- chromatography --; line 62, delete "chromogen" and insert -- chromagen --;

Column 7, line 6, delete "nurethynodrel" and insert -- norethynodrel --; line 64, delete "degredation" and insert -- degradation --;

Column 8, line 10, delete "Detectible" and insert -- Detectable --; line 15, delete "particle" and insert -- particles --; line 51, delete "autoadiograms" and insert --autoradiograms --; line 63, delete "analagous" and insert -- analogous --;

Column 9, line 41, delete "DEAF" and insert -- DEAE --;

Column 11, line 26, delete "immuno assay" and insert -- immunoassay --; line 34, delete "horse radish" and insert -- horseradish --; line 49, delete "analagous" and insert -- analogous --;

UNITED STATES PATENT AND TRADEMARK OFFICE
CERTIFICATE OF CORRECTION

PATENT NO. : 4,742,000

DATED : May 3, 1988

INVENTOR(S) : Geoffrey L. Greene

It is certified that error appears in the above-identified patent and that said Letters Patent is hereby corrected as shown below:

Column 13, Table 3, footnote number 1, delete "progesteron" and insert -- progesterone --;

Column 15, line 57, delete "detectible" and insert -- detectable --; line 58, delete "detectible" and insert -- detectable --; line 60, delete "detectible" and insert -- detectable --; line 62, delete "detectible" and insert -- detectable --; line 64, delete "detectible" and insert -- detectable --; lines 66-67, delete "noncavalently" and insert -- noncovalently --; line 67, delete "convalently" and insert -- covalently --;

Column 16, line 5, delete "detectible" and insert -- detectable --; line 20, delete "detactable" and insert -- detectable --; line 51, delete "incoulated" and insert -- inoculated --;

Column 18, line 7, delete "detactable" and insert -- detectable --.

Signed and Sealed this

Twentieth Day of September, 1988

Attest:

DONALD J. QUIGG

Attesting Officer

Commissioner of Patents and Trademarks

UNITED STATES PATENT AND TRADEMARK OFFICE
CERTIFICATE OF CORRECTION

PATENT NO. : 4,742,000

DATED : May 3, 1988

INVENTOR(S) : Geoffrey L. Greene

It is certified that error appears in the above-identified patent and that said Letters Patent is hereby corrected as shown below:

At column 1, line 5, please insert -- This invention was made with government support under grants CA-02897 and HD-17103 awarded by the National Institutes of Health. The government has certain rights in the invention. --.

Signed and Sealed this

Twentieth Day of April, 1993

Attest:

MICHAEL K. KIRK

*Attesting Officer*    Acting Commissioner of Patents and Trademarks